US008758795B2

(12) United States Patent
Siegel et al.

(10) Patent No.: US 8,758,795 B2
(45) Date of Patent: *Jun. 24, 2014

(54) POLYMER-BASED SURGICALLY IMPLANTABLE HALOPERIDOL DELIVERY SYSTEMS AND METHODS FOR THEIR PRODUCTION AND USE

(75) Inventors: Steven J. Siegel, Berwyn, PA (US); Karen I. Winey, Philadelphia, PA (US); Raquel E. Gur, Philadelphia, PA (US); Robert H. Lenox, Califon, NJ (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 433 days.

This patent is subject to a terminal disclaimer.

(21) Appl. No.: 12/582,615

(22) Filed: Oct. 20, 2009

(65) Prior Publication Data

US 2010/0104618 A1 Apr. 29, 2010

Related U.S. Application Data

(63) Continuation of application No. 10/046,504, filed on Oct. 19, 2001, now Pat. No. 7,666,445.

(60) Provisional application No. 60/242,304, filed on Oct. 20, 2000.

(51) Int. Cl.
 *A61F 2/00* (2006.01)
 *A61K 31/445* (2006.01)

(52) U.S. Cl.
 USPC .......................................... 424/423; 514/327

(58) Field of Classification Search
 USPC .......................................... 424/423; 514/327
 See application file for complete search history.

(56) References Cited

U.S. PATENT DOCUMENTS

| 4,351,337 | A | | 9/1982 | Sidman |
|---|---|---|---|---|
| 4,450,150 | A | | 5/1984 | Sidman |
| 4,874,612 | A | | 10/1989 | Deasy |
| 4,883,666 | A | | 11/1989 | Sabel et al. |
| 5,047,536 | A | | 9/1991 | Nichols |
| 5,490,962 | A | | 2/1996 | Cima et al. |
| 5,601,835 | A | | 2/1997 | Sabel et al. |
| 5,629,008 | A | | 5/1997 | Lee |
| 5,648,096 | A | * | 7/1997 | Gander et al. ................ 424/489 |
| 5,654,008 | A | | 8/1997 | Herbert et al. |
| 5,656,299 | A | | 8/1997 | Kino et al. |
| 5,665,428 | A | | 9/1997 | Cha et al. |
| 5,770,231 | A | | 6/1998 | Mesens |
| 5,792,477 | A | | 8/1998 | Rickey et al. |
| 5,817,343 | A | | 10/1998 | Burke |
| 5,871,778 | A | | 2/1999 | Kino et al. |
| 5,965,168 | A | | 10/1999 | Mesens |
| 5,989,463 | A | | 11/1999 | Tracy et al. |
| 6,004,573 | A | | 12/1999 | Rathi et al. |
| 6,077,843 | A | | 6/2000 | Francois et al. |
| 6,086,908 | A | | 7/2000 | Gopferich |
| 6,110,921 | A | | 8/2000 | Mesens |
| 6,117,949 | A | | 9/2000 | Rathi et al. |
| 6,130,200 | A | | 10/2000 | Brodbeck et al. |
| 6,143,314 | A | | 11/2000 | Chandrashekar |
| 6,147,072 | A | * | 11/2000 | Bymaster et al. ............. 514/220 |
| 6,166,173 | A | | 12/2000 | Mao et al. |
| 6,197,764 | B1 | | 3/2001 | Bradley et al. |
| 6,201,072 | B1 | | 3/2001 | Rathi et al. |
| 6,303,137 | B1 | * | 10/2001 | Dittgen et al. ................ 424/426 |
| 6,319,512 | B1 | | 11/2001 | Rothen-Weinhold et al. |
| 6,322,797 | B1 | | 11/2001 | Mao et al. |
| 6,368,362 | B1 | | 4/2002 | Pedemonte et al. |
| 6,544,559 | B2 | | 4/2003 | Mesens |
| 6,548,484 | B1 | * | 4/2003 | Christian .......................... 514/25 |
| 6,750,341 | B2 | | 6/2004 | Krochmal et al. |
| 6,803,055 | B2 | | 10/2004 | Mesens |
| 7,004,977 | B2 | * | 2/2006 | Ashman ..................... 623/23.73 |
| 8,221,788 | B2 | * | 7/2012 | Viragh et al. ................. 424/465 |
| 8,329,203 | B2 | * | 12/2012 | Siegel et al. ................. 424/423 |
| 2001/0005719 | A1 | | 6/2001 | Von Borstel |
| 2002/0179096 | A1 | | 12/2002 | Siegel et al. |
| 2006/0159721 | A1 | | 7/2006 | Siegel et al. |
| 2008/0305140 | A1 | | 12/2008 | Siegel et al. |
| 2009/0297572 | A1 | | 12/2009 | Siegel et al. |

FOREIGN PATENT DOCUMENTS

| EP | 669128 | 1/2000 |
|---|---|---|
| JP | S58-216117 A | 12/1983 |
| JP | S64-071823 A | 3/1989 |
| JP | H01-216917 A | 8/1989 |
| JP | H04-0217914 A | 8/1992 |
| JP | 2003-534268 A | 6/2004 |

(Continued)

OTHER PUBLICATIONS

Cheng et al., "A poly(D,L-lactide-co-glycolide) microsphere depot system for delivery of haloperidol," in Journal of Controlled Release 55 (1998) 203-212.*

(Continued)

*Primary Examiner* — Blessing M Fubara
(74) *Attorney, Agent, or Firm* — Mark S. Cohen; Pearl Cohen Zedek Latzer Baratz LLP

(57) ABSTRACT

Surgically implantable drug delivery systems for long-term delivery of haloperidol containing a biodegradable polymer and haloperidol fabricated into the surgically implantable drug delivery systems via solvent casting and compression molding are provided. Also provided are methods for producing the surgically implantable drug delivery systems and methods for using these systems in the treatment of psychotic disorders such as schizophrenia.

9 Claims, No Drawings

(56) References Cited

FOREIGN PATENT DOCUMENTS

| WO | WO 94/10982 | 5/1994 |
|---|---|---|
| WO | WO 95/13814 | 5/1995 |
| WO | WO 97/41837 | 11/1997 |
| WO | WO 02/00137 | 1/2002 |
| WO | WO 03/000156 | 1/2003 |
| WO | WO 01/089482 | 3/2003 |
| WO | WO 03/020200 | 3/2003 |
| WO | WO 03/020245 | 3/2003 |
| WO | WO 2004/078160 | 9/2004 |
| WO | WO 2005/000277 | 1/2005 |
| WO | WO 2005/070332 | 8/2005 |

OTHER PUBLICATIONS

Adams CE, Fenton MK, Quraishi S, David AS (2001) Systematic meta-review of depot antipsychotic drugs for people with schizophrenia. Br J Psychiatry 179:290-299.
Anderson, et al. (1997) Biodegradation and biocompatibility of PLA and PLGA microspheres. Adv Drug Delivery Rev 28:5-24.
Ayuso-Gutierrez, et al. (1997) Factors influencing relapse in the long-term course of schizophrenia. Schizophr Res 28:199-206.
Benelli, et al. (1998) Clonazepam microencapsulation in poly-D, L-lactide-co-glycolide microspeheres. J. Micorenscapsulation 15(4):431-443.
Boccuzzi et al. (2001) Utilization of oral hypoglycemic agents in a drug-insured U.S. population. Diabetes Care. Aug;24(8):1411-5.
Buckland, et al. (1993) Both splicing variants of the dopamine D2 receptor mRNA are up-regulated by antipsychotic drugs. Neurosci Lett 150:25-28.
Chen, et al. (2005) Microarray analysis of differentially expressed genes in rat frontal cortex under chronic risperidone treatment. Neuropsychopharmacology 30:268-277.
Cheng, et al. (1998) a poly (D,L-lactide-co-glycolide) microsphere depot system for delivery of haloperidol. J. Controlled Release 55(2-3):203-212.
Cheng, et al. (2000) Schizophrenia and Drug Delivery Systems. J Drug Targeting 8(2):107-117.
Chui et al. (2003) Association between adherence to diuretic therapy and health care utilization in patients with heart failure. Pharmacotherapy. Mar;23(3):326-32.
Corriss, et al. (1999) Interactive risk factors for treatment adherence in a chronic psychotic disorders population. Psychiatry Res 89:269-274.
Csernansky (2003) Treatment of schizophrenia: preventing the progression of disease. Psychiatr Clin North Am 26:367-379.
Dash, et al. (1998) Therapeutic applications of implantable drug delivery systems. J Pharmacol Toxicol Methods 40:1-12.
Davis, et al. (2003) A meta-analysis of the efficacy of second-generation antipsychotics. Arch Gen Psychiatry 60:553-564.
Dorph-Petersen, et al. (2004) Stereological analysis of the mediodorsal thalamic nucleus in schizophrenia: volume, neuron number, and cell types. J Comp Neurol 472:449-462.
Elmer, et al. (1996) Cocaine cross-sensitization to dopamine uptake inhibitors: unique effects of GBR12909. Pharmacol Biochem Behav 53:911-918.
Fischel-Ghodsian, et al. (1993) Analysis of drug release kinetics from degradable polymeric devices. J Drug Target.1(1):51-57.
Foss, et al. (2004) Development of acrylic-based copolymers for oral insulin delivery. Eur J Pharm Biopharm 57:163-169.
Foster and Goa (1998) Risperidone. A pharmacoeconomic review of its use in schizophrenia.Pharmacoeconomics. Jul;14(1):97-133.
Frank, et al. (2005) Controlled release from bioerodible polymers: effect of drug type and polymer composition. J Controlled Release 102:333-344.
Freiberg and Zhu (2004) Polymer microspheres for controlled drug release. Int J Pharm. Sep. 10;282(1-2):1-18.
Gander, et al. (2001) Polymers as a platform for drug delivery: Reviewing our current portfolio on poly(lactide-co-glycolide) (PLGA) microspheres. CHIMIA 55:212-217.

Geddes, et al. (2000) Atypical antipsychotics in the treatment of schizophrenia: systematic overview and meta-regression analysis. BMJ 321:1371-1376.
Goss, et al. (1991) Haloperidol treatment increases D2 dopamine receptor protein independently of RNA levels in mice. Life Sci 48:1015-1022.
Grayson, et al. (2005) Size and temperature effects on poly(lactic-co-glycolic acid) degradation and microreservoir device performance, Biomaterials 26:2137-2145.
Harrison and Goa (2004) Long-acting risperidone: a review of its use in schizophrenia. CNS Drugs.; 18(2):113-32.
Heller, (1979) Controlled drug release by polymer dissolution. II: Enzyme-mediated delivery device. J Pharm Sci. 68(7):919-21.
Higuchi T., (1961) Rate of release of medicaments from ointment bases containing drugs in suspensions. J. Pharm. Sci. 50:874-875.
Holy, et al. (2001) Optimizing the sterilization of PLGA scaffolds for use in tissue engineering. Biomaterials 22:25-31.
Hussain (2001) Fluorometric method for the simultaneous quantitation of differently-sized nanoparticles in rodent tissue. Int J Pharm 214:55-61.
Irani, et al. (2004) Patient attitudes towards surgically implantable, long-term delivery of psychiatric medicine. Neuropsychopharmacology 29:960-968.
Jain, et al. (2000) Controlled delivery of drugs from a novel injectable in situ formed biodegradable PLGA microsphere system. J Microencapsulation 17(3):343-62.
Jeong, et al. (2003) Preparation of poly(DL-lactide-co-glycolide) microspheres encapsulating all-trans retinoic acid. Int J Pharm 259:79-91.
Kane (1999) Olanzapine in the long-term treatment of schizophrenia. Br J Psychiatry Suppl: (37) 26-29.
Kane, et al. (1998) Guidelines for depot antipsychotic treatment in schizophrenia. European Neuropsychopharmacology Consensus Conference in Siena, Italy. Eur Neuropsychopharmacol 8:55-66.
Kane, et al. (2002) Efficacy and safety of aripiprazole and haloperidol versus placebo in patients with schizophrenia and schizoaffective disorder. J Clin Psychiatry 63:763-771.
Karow, et al. (2002) Subjective well-being and quality of life under atypical antipsychotic treatment. Psychopharmacology (Berl) 162:3-10.
Keefe, et al. (2004) Comparative effect of atypical and conventional antipsychotic drugs on neurocognition in first-episode psychosis: a randomized, double-blind trial of olanzapine versus low doses of haloperidol. Am J Psychiatry 161:985-995.
Keith, et al. (2003) Partial compliance and patient consequences in schizophrenia: our patients can do better. J Clin Psychiatry 64:1308-1315.
Kitchell, et al. (1985) Poly (lactic/glycolic acid) biodegradable drug-polymer matrix systems. Methods Enzymol. 112:436-48.
Klavon, et al. (1990) Insertion site complications during the first year of NORPLANT use. Contraception 41:27-37.
Knable, et al. (1997) Extrapyramidal side effects with risperidone and haloperidol at comparable D2 receptor occupancy levels. Psychiatry Res 75:91-101.
Knegtering, et al. (2005) Predominant role of the 9-hydroxy metabolite of risperidone in elevating blood prolactin levels. Am J Psychiatry 162:1010-1012.
Kohler, et al. (1994) A new animal model of dopamine supersensitivity using s.c. implantation of haloperidol releasing polymers. Neuroscience Letters 170(1):99-102.
Kulkarni, et al. (1971) Biodegradable poly(lactic acid) polymers. 5(3):169-81.
Kusumi, et al. (2000) Differential effects of subchronic treatments with atypical antipsychotic drugs on dopamine D2 and serotonin 5-HT2A receptors in the rat brain. J Neural Transm 107:295-302.
Lambert, et al. (2003) Pharmacological approaches to the management of schizophrenia. Med J Aust 178 Suppl: S57-61.
Larobina, et al. (2002) Mechanistic understanding of degradation in bioerodible polymers for drug delivery. AICHE J 48:2960-2970.
Lelas, et al. (2004) Anxiolytic-like effects of the corticotropin-releasing factorl (CRF1) antagonist DMP904 [4-(3-pentylamino)-2,7-dimethyl-8-(2-methyl-4-methoxyphenyl)-pyrazolo-[1,5-a]-

(56) References Cited

OTHER PUBLICATIONS pyrimidine] administered acutely or chronically at doses occupying central CRF1 receptors in rats. J Pharmacol Exp Ther 309:293-302.

Lewis, et al. (2001a) Lamina-specific deficits in parvalbumin-immunoreactive varicosities in the prefrontal cortex of subjects with schizophrenia: evidence for fewer projections from the thalamus. Am J Psychiatry 158:1411-1422.

Lewis, et al. (2001b) Service use and costs of treating schizophrenia with atypical antipsychotics. J Clin Psychiatry 62:749-756.

Leysen, et al. (1994) Risperidone: a novel antipsychotic with balanced serotonin-dopamine antagonism, receptor occupancy profile, and pharmacologic activity. J Clin Psychiatry 55 Suppl:5-12.

Li, et al. (1996) Hydrolytic degradation of poly (D,L-lactic acid) in the presence of caffeine base. J. Control. Release 40:41-53.

Lilly, et al. (1998) A physiologically based pharmacokinetic description of the oral uptake, tissue dosimetry, and rates of metabolism of bromodichloromethane in the male rat. Toxicol Appl Pharmacol 150:205-217.

Linhardt (1989) "Biodegradable Polymers for Controlled Release of Drugs" Controlled Release of Drugs, Rosoff, Ed., New York: VCH Publishers, Chapter 2, p. 53-83.

Lu et al. (2000) In vitro and in vivo degradation of porous poly(DL-lactic-co-glycolic acid) foams. Biomaterials. Sep; 21(18):1837-45.

Martin, et al. (2003) Clinical experience with the long-acting injectable formulation of the atypical antipsychotic, risperidone. Curr Med Res Opin 19:298-305.

McCombs, et al. (1999) Use patterns for antipsychotic medications in medicaid patients with schizophrenia. J Clin Psychiatry 60 Suppl 19:5-11; discussion 12-13.

McQuade, et al. (2004) A comparison of weight change during treatment with olanzapine or aripiprazole: results from a randomized, double-blind study. J Clin Psychiatry 65 Suppl 18:47-56.

Meltzer (1995) The role of serotonin in schizophrenia and the place of serotonin-dopamine antagonist antipsychotics. J Clin Psychopharmacol 15:2S-3S.

Menzin, et al. (2003) Treatment adherence associated with conventional and atypical antipsychotics in a large state medicaid program. Psychiatr Serv 54:719-723.

Metzger, et al. "Pharmacokinetic and behavioral characterization of a long-term antipsychotic delivery system in rodents and rabbits" Psychopharmacology Psychopharmacology (Berl). Feb. 2007; 190(2):201-11.

Miller-Chou, et al. (2003) A reviews of polymer dissolution. Progress Pol Sci 28:1223-1270.

Narasimhan, et al. (1997) Molecular analysis of drug delivery systems controlled by dissolution of the polymer carrier. J Pharma Sci 86:297-304.

Nasrallah, et al. (2002) Efficacy, safety, and tolerability of quetiapine in patients with schizophrenia. J Clin Psychiatry 63 Suppl 13:12-20.

Nasrallah, et al. (2004) Atypical antipsychotics and metabolic dysregulation: evaluating the risk/benefit equation and improving the standard of care. J Clin Psychopharmacol 24:S7-14.

Natsugoe, et al. (1960) Controlled Release of Cisplatin Incorporated into Biodegradable Poly-D, L-Lactic Acid. Anticancer Research 17(3C):1957-60.

Nyberg, et al. (1996) Positron emission tomography of in-vivo binding characteristics of atypical antipsychotic drugs. Review of D2 and 5-HT2 receptor occupancy studies and clinical response. Br J Psychiatry Suppl:40-44.

Okada, et al. (1995) Biodegradable microspheres in drug delivery. Crit Rev Ther Drug Carrier Syst 12:1-99.

Panyam, et al. (2003) Biodegradable nanoparticles for drug and gene delivery to cells and tissue. Adv Drug Delivery Rev 55:329-347.

Ramaswamy, et al. (2004) Aripiprazole possibly worsens psychosis. Int Clin Psychopharmacol 19:45-48.

Reeves, et al. (2004) Worsening schizoaffective disorder with aripiprazole. Am J Psychiatry 161:1308.

Reuss, et al. (2001) Atypical neuroleptic drugs downregulate dopamine sensitivity in rat cortical and striatal astrocytes. Mol Cell Neurosci 18:197-209.

Robinson, et al. (2002) Predictors of medication discontinuation by patients with first-episode schizophrenia and schizoaffective disorder. Schizophr Res 57:209-219.

Ron, et al. (1991) "Erodible Systems" *Treatise on Cont. Drug Del.* 199-217.

Roskos, et al. (1997) "Degradable controlled release systems useful for protein delivery" in Protein Delivery: Physical Systems, Sanders and Hendren eds., Plenum press, New York, Chapter 2, 45-92.

Sabel, et al. (1990) Levodopa delivery from controlled-release polymer matrix: delivery of more than 600 days in vitro and 225 days of elevated plasma levels after subcutaneous implantation in rats. J Pharmacol Exp Ther 255:914-922.

Sarma, et al. (1995) Neurovascular injury during removal of levonorgestrel implants. Am J Obstet Gynecol 172:120-121.

Schotte, et al. (1996) Risperidone compared with new and reference antipsychotic drugs: in vitro and in vivo receptor binding. Psychopharmacology (Berl) 124:57-73.

Seeman MV (2001) Clinical trials in psychiatry: do results apply to practice? Can J Psychiatry 46:352-355.

Sharma, et al. (2003) Cognitive function in schizophrenia. Deficits, functional consequences, and future treatment. Psychiatr Clin North Am 26:25-40.

Siegel (2007) Extended release drug delivery strategies in psychiatry: Theory to practice. Psychiatry.

Siegel, et al. (2002) Surgically implantable long-term antipsychotic delivery systems for the treatment of schizophrenia. Neuropsychopharmacology 26:817-823.

Siegel, et al. (2006) Effect of drug type on the degradation rate of PLGA Matrices. Eur J Pharm Biopharm. 64(3):287-93.

Siepmann, et al. (2001) Mathematical modeling of bioerodible, polymeric drug delivery systems. Adv Drug Delivery Rev 48:229-247.

Simpson, et al. (2004) Randomized, controlled, double-blind multicenter comparison of the efficacy and tolerability of ziprasidone and olanzapine in acutely ill inpatients with schizophrenia or schizoaffective disorder. Am J Psychiatry 161:1837-1847.

Strakowski, et al. (2003) Atypical antipsychotics in the treatment of bipolar disorder. Expert Opin Pharmacother 4:751-760.

Sung, et al. (1998) Controlled release of nalbuphine prodrugs from biodegradable polymeric matrices: influence of prodrug hydrphillicity and polymer composition. Int. J. Pharm. 172:17-25.

Svarstad, et al. (2001) Using drug claims data to assess the relationship of medication adherence with hospitalization and costs. Psychiatr Serv 52:805-811.

Swainston Harrison, et al. (2004) Aripiprazole: a review of its use in schizophrenia and schizoaffective disorder. Drugs 64:1715-1736.

Swerdlow, et al. (1994) Assessing the validity of an animal model of deficient sensorimotor gating in schizophrenic patients. Arch Gen Psychiatry 51:139-154.

Tarazi, et al. (2002) Long-term effects of olanzapine, risperidone, and quetiapine on serotonin 1A, 2A and 2C receptors in rat forebrain regions. Psychopharmacology (Berl) 161:263-270.

Teich (2003) Side effects of ziprasidone. Am J Psychiatry 160:1355-1356.

Velligan, et al. (2003) Psychopharmacology: perspectives on medication adherence and atypical antipsychotic medications. Psychiatr Serv 54:665-667.

Visco, et al. (1999) Observed patient compliance with a structured outpatient bladder retraining program. Am J Obstet Gynecol 181:1392-1394.

Wada, et al. (1991) in vitro evaluation of sustained drug release from biodegradable elastomer. Pharm Res. 8(10):1292-1296.

Wang, et al. (2000) Synthesis, characterization, biodegradation, and drug delivery application of biodegradable lactic/glycolic acid polymers: I. Synthesis and characterization. J Biomater Sci Polym Ed. 11(3):301-18.

Yasui-Furukori, et al. (2001) Different enantioselective 9-hydroxylation of risperidone by the two human CYP2D6 and CYP3A4 enzymes. Drug Metab Dispos 29:1263-1268.

Zheng, et al. (1998) High-performance liquid chromatography-mass spectrometry-mass spectrometry analysis of morphine and morphine metabolites and its application to a pharmacokinetic study in male Sprague-Dawley rats. J Pharm Biomed Anal 16:971-980.

(56) References Cited

OTHER PUBLICATIONS

Barichello et al. "Encapsulation of Hydrophilic and Lipophilic Drugs in PLGA Nanoparticles by the Nanoprecipitation Method", vol. 25. No. 4, pp. 471-476, (1999).

Budhian et al. "Production of haloperidol loaded PLGA nanoparticles for extended controlled drug release of haloperidol" Journal of Microencapsulation, vol. 22, Issue 7, pp. 773-785 Nov. 2005.

Budhian et al. "Haloperidol-loaded PLGA nanoparticles: Systematic study of particle size and drug content" International Journal of Pharmaceutics 336 ,367-375, (2007).

Choi et al. "Development of Drug-Loaded PLGA Microparticles with Different Release Patterns for Prolonged Drug Delivery" Bull. Korean Chem. Soc. vol. 32, No. 3, 867, (2011).

Chorny et al. "Study of the drug release mechanism from tyrphostin AG-1295-loaded nanospheres by in situ and external sink methods" Journal of Controlled ReleaseVolume 83, Issue 3, pp. 401-414, Oct. 30, 2002.

Kiortsis et al. "Drug release from tableted wet granulations comprising cellulosic (HPMC or HPC) and hydrophobic component" Eur J Pharm Biopharm.; 59(1):73-83, Jan. 2005.

Chinese Office Action Application No. 200580039021.3 Dated Oct. 9, 2010.

Japanese Office Action Application No. 2006-549540 Dated Feb. 15, 2011.

European Search Report Application No. PCT/US2006027894 Dated Oct. 10, 2011.

Domb et al "Degradable Polymers for Site-specific Drug Delivery" Polymers for Advanced Technologies, vol. 3, pp. 279-292, 1992.

Santos et al "Clinical implications of determination of plasma haloperidol levels" Acta Psychiatr Scand 1989: 79:348-254.

Deng X et al, "In vitro degradation and release profiles for poly-dl-lactide-poly(ethylene glycol) microspheres containing human serum albumin" J Control Release 71(2):165-73, 2001.

J de Kanel et al., "A simple technique for surface area determination", J Phys E: Sci Instrum 12: 272-273, 1979.

Foster RH, "Risperidone. A pharmacoeconomic review of its use in schizophrenia" (1998) Pharmacoeconomics 14: 97-133.

Hoffman HS, "Acoustic Variables in the Modification of Startle Reaction in the Rat" (1965) J Comp Physiol Psychol 60:53-58.

Mansbach RS, "Effects of phencyclidine and phencyclidine biologs on sensorimotor gating in the rat" (1989). Neuropsychopharmacol 2: 299-308.

Swerdlow NR et al, "Effects of spiperone, raclopride, SCH 23390 and clozapine on apomorphine inhibition of sensorimotor gating of the startle response in the rat" (1991). J Pharmacol Exp Ther 256: 530-536.

Swerdlow NR et al, "Discrepant findings of clozapine effects on prepulse inhibition of startle: is it the route or the rat?" Neuropsychopharmacol 18: 50-56, 1998.

Braff DL, "Sensorimotor gating and schizophrenia. Human and animal model studies" (1990) Arch Gen Psychiatry 47: 181-188.

Elmer GI, Brockington A et al, "Cocaine cross-sensitization to dopamine uptake inhibitors: unique effects of GBR12909" Pharmacol Biochem Behav 53: 911-918, 1996.

Adler et al, "Schizophrenia, sensory gating, and nicotinic receptors", Schizophr Bull 24: 189-202, 1998.

Freedman et al, "Schizophrenia and nicotinic receptors", Harv Rev Psychiatry 2: 179-192, 1994.

Wurzburger et al, "A new radioimmunoassay for haloperidol: direct measurement of serum and striatal concentrations" J Pharmacol Exp Ther 217: 757-763, 1998.

Bacopoulos et al., "Chronic haloperidol or fluphenazine: Effects on dopamine metabolism in brain, cerebrospinal fluid, and plasma of cercopithecus aethiops (vervet monkey)", J Pharmacol Exp Ther 212: 1-5, 1980.

Jibiki et al., "Effective Clinical Response at Low Plasma Levels of Haloperidol in Japanese Schizophrenics with Acute Psychotic State", Jpn J Psychiatry Neurol 47: 627-629, 1993.

* cited by examiner

POLYMER-BASED SURGICALLY IMPLANTABLE HALOPERIDOL DELIVERY SYSTEMS AND METHODS FOR THEIR PRODUCTION AND USE

CROSS-REFERENCE TO RELATED APPLICATIONS

This application is a continuation of U.S. Utility application Ser. No. 10/046,504, filed Oct. 19, 2001 now U.S. Pat. No. 7,666,445, that claims the benefit of priority from U.S. Provisional Application Ser. No. 60/242,304, filed Oct. 20, 2000, both of which are incorporated by reference herein in their entirety.

FIELD OF THE INVENTION

The invention relates to surgically implantable drug delivery systems for the long-term delivery of antipsychotic drugs, and in particular haloperidol. The surgically implantable drug delivery systems of the present invention comprise a biodegradable polymer, preferably a lactide-co-glycolide copolymer, and an antipsychotic drug, preferably haloperidol, fabricated into an implant via solvent casting and compression molding. As demonstrated herein, these formulations, when implanted underneath the skin, release an effective amount of the antipsychotic drug over a period of months. Also provided in the present invention are methods for producing and using these surgically implantable drug delivery systems in the treatment of patients with psychotic disorders such as schizophrenia.

BACKGROUND OF THE INVENTION

While much research regarding the treatment of schizophrenia has focused on new pharmaceutical compounds, a major correctable cause for treatment resistance remains nonadherence with prescribed medication (Fenton et al. Schizophr. Bull. 1997 23(4):637-51; Kane, J. J. Clin. Psychopharmacol. 1985 5(3 Suppl):22s-27s). Approximately 50% of patients with schizophrenia and other chronic psychotic conditions are believed to be poorly adherent with prescribed medication (Young et al. Bull. Am. Acad. Psychiatry Law 1986 14(2):105-22). A controlled study to measure adherence with a detectable marker reported that 80% of patients with schizophrenia do not take medications as prescribed (Kapur et al. Schizophr. Res. 1991 6(1):49-53). Studies of relapsed patients have reported only 30% to meet the criteria for good adherence in the months prior to admission (Bergen et al. Aust. N Z J. Psychiatry 1998 32(6):815-22; Razali et al. Acta Psychiatr. Scand. 1995 91(5):331-5).

Therapeutic failure secondary to nonadherence often results in deterioration in social function and more intensive interventions including rehospitalization, such that nonadherence was the most important predictor of rehospitalization in a state hospital population (Casper, E. S. and Regan, J. R. Can. J. Psychiatry 1993 38(10):657-61). Furthermore, length of stay upon rehospitalization is shorter among medication adherent patients and they are less likely to require involuntary admission (McEvoy et al. J. Nerv. Ment. Dis. 1984 172 (7):412-6). Without antipsychotic treatment, 75% of patients with schizophrenia relapse within one year of first presentation, compared to 15% of treated patients (Ayuso-Gutierrez, J. L and del Rio Vega, J. M. Schizophr. Res. 1997 28(2-3): 199-206; Davis, J. M. and Andriukaitis, S. J. Clin. Psychopharmacol. 1986 6(1 Suppl):2S-10S). Discontinuation of antipsychotic medication also has been disclosed to increase risk of relapse approximately 5-fold (Robinson et al. Arch. Gen. Psychiatry 1999 56(3):241-7). Similarly, a study that followed first episode patients for 2 years found relapse rates up to 90% for non-medicated patients (Ram et al. Schizophr. Bull. 1992 18:185-207). Furthermore, good adherence following discharge from the hospital can reduce recidivism from 73% to 27% within one year (Gaebel, W. and Pietzeker, A. Pharmacopsychiatry 1985 18(3):235-9).

Consequences of medication nonadherence can extend beyond the health of the patient. While the majority of people with schizophrenia do not engage in violent behavior, a subset of patients display aggression during periods of psychosis (Casper, E. S. and Regan, J. R. Can. J. Psychiatry 1993 38(10):657-61; Lindqvist, P. and Allebeck, P. Br. J. Psychiatry 1990 157:345-50; Mitchell, E. W. Med. Sci. Law 1999 39(1):23-30; Tam et al. Psychiatr. Serv. 1996 47(1):86-8).

Efforts to increase medication adherence have incorporated behavioral and psychoeducational programs, family interventions and intensive supportive services (Agarwal et al. Int. J. Soc. Psychiatry 1998 44(2):92-106; Amador, X. F. and Gorman, J. M. Psychiatric. Clin. North Am. 1998 21(1): 27-42; Bustillo et al. Harv. Rev. Psychiatry 1999 6(5):229-40; Yong et al. Bull Am. Acad. Psychiatry Law 1986 14(2):105-22).

Pharmacological approaches to improved adherence include improving tolerability and efficacy of antipsychotic medication (Bustillo et al. Harv. Rev. Psychiatry 1999 6(5): 229-40; Kane, J. Br. J. Psychiatry Suppl. 1999 37:26-9; Kasper, S. Int. Clin. Psychopharmacol. 1998 13 Suppl 3:S71-7; Mauskopf et al. J. Clin. Psychiatry 1999 60(Suppl 19):14-9) through development of new agents and administration of monthly depot preparations of existing agents.

Decreased rates of discontinuation were reported for a newer agent, olanzapine, than an older one (haloperidol) (Tran et al. J. Clin. Psychiatry 1997 June 58(5):205-11; Tran et al. J. Clin. Psychiatry 1997 June 58(6):275). However, newer agents have been reported to have additional side effects including weight gain, sedation, drooling, Q-T prolongation and agranulocytosis (Campbell et al. Br. J. Clin. Pharmacol. 1999 47(1):13-22; Wetterling, T. and Mussigbrodt, H. E. J. Clin. Psychopharmacol. 1999 19(4):316-21).

Monthly depot preparations have been reported as an effective means to decrease relapse and rehospitalization (Gerlach, J. Int. Clin. Psychopharmacol. 1995 9 Suppl 5:17-20). Treatment for noncompliant patients with depot formulations (Haldol-decanoate) is much less expensive per year than oral preparations of newer neuroleptics (risperidone; Galzer, W. M. and Ereshefsky, L. J. Clin. Psychiatry 1996 57(8):337-45). However, a 7-year study of depot medication found a significant number of patients fail to comply with monthly injections and discontinuation linked to relapse (Curson et al. Br. J. of Psychiatry 1985 146:469-74). Therefore, while depot medication improves adherence initially, many patients still become nonadherent (Weiden et al. Psychiatric Services 1995 46(10):1049-54).

In contrast, a surgically implantable preparation can last for many months, providing patients with symptomatic improvement and possibly delayed disease progression for periods of time never before possible. Additionally, in the event of unacceptable side effects, implants can be removed. This offers a degree of reversibility not presently available with depot formulations. Further, surgically implantable formulations can be employed as a safety net in combination with oral dosing to achieve adjustments as clinically indicated.

Surgically implantable drug delivery systems have been applied in contraception, drug addiction, chemotherapy and pain management. The most widely used, NORPLANT®, (Wyeth Laboratories Inc. Philadelphia, Pa.) provides 5 years of contraception using levonorgestrel in silicon tubing, allowing for steady state diffusion of active ingredient (Woutersz, T. B. Inter. J. of Fertility 1991 3(51):51-6). Silicon-based delivery systems are ideal for hormonal delivery due to picogram daily dose requirements. However, this range is not suited for antipsychotics due to slow rates of release.

Polymer based delivery systems release milligram range daily dosing required for antipsychotic medications. The polymers used in these systems were initially used in surgical applications (Kulkarni et al. Arch. Surg. 1966 93(5):839-43), but have been modified to integrate medications to form surgically implantable or injectable formulations that release drug over weeks to months. These materials are divided into two categories, namely non-erodible and bioerodible polymers.

Non-erodible polymers release drug primarily by diffusion while leaving the delivery matrix in place. Non-erodible ethylene vinyl acetate (EVA) is a widely used non-erodible material. Subcutaneous delivery of haloperidol has been demonstrated in rats up to 250 days using EVA (Kohler et al. Neuroscience Letter 1994 170(1):99-102). This preparation delivered steady state levels of haloperidol in vitro with physiologic effects on striatal dopamine receptor regulation.

Bioerodible polymers release medication by erosion of the polymer matrix and diffusion of drug through the remaining polymer matrix. Examples of bioerodible polymers include, but are not limited to, high molecular weight polymers of lactic and glycolic acids, which can be used individually or in lactide-co-glycolide copolymers (PLGA). Advantages of PLGA copolymers include low antigenicity and clearance of breakdown products (lactic and glycolic acid) through the Krebs cycle. These materials have been used in microspheres for injectable depot preparations of chlorpromazine (Gao et al. J. Microencapsul. 1998 15(1):75-83) and haloperidol (Cheng et al. J. Controlled Release 1998 55(2-3):203-12) and are now in clinical use with risperidone (http://www.alkermes.com/index news.html, Apr. 22, 1999). Microspheres are delivered as a suspension, and last approximately 2 weeks.

Various drug delivery devices comprising biodegradable polymers are disclosed generally in, for example, U.S. Pat. No. 5,665,428, U.S. Pat. No. 5,817,343, U.S. Pat. No. 5,871, 778, U.S. Pat. No. 5,989,463, U.S. Pat. No. 6,004,573, U.S. Pat. No. 6,117,949, U.S. Pat. No. 6,143,314, and U.S. Pat. No. 6,201,072. These patents each contain an extensive list of possible active agents or therapeutic classes of drugs which are suggested to be deliverable via the drug delivery device.

In addition, U.S. Pat. No. 4,883,666 teaches encapsulation of a compound for treatment of ischemic, metabolic, congenital or degenerative disorders of the central or peripheral nervous system within an implantable biocompatible polymeric device. At col. 13, lines 51-59, it is taught that polymer implants with antipsychotics can be used to treat schizophrenia. Polymer implants used in the examples of the '666 patent all comprised the non-erodible polymer ethylene vinyl acetate (EVA) and dopamine. Further, coating of the implant with a layer of EVA except for one or two holes was required for linear release. Use of bioerodible polymers in implants is suggested at col. 7, line 60 of this patent. However, no examples of implants comprising bioerodible polymers and specific therapeutic agents are taught.

U.S. Pat. No. 5,601,835 teaches similar formulations to those taught in U.S. Pat. No. 4,883,666. However, these formulations are implanted directly into the central nervous system. Again, no examples of implants comprising bioerodible polymers and specific therapeutic agents are taught.

As shown herein, however, not all pharmaceutical agents, and more particularly antipsychotic agents, are amenable to delivery via systems comprising bioerodible polymers.

SUMMARY OF THE INVENTION

An object of the present invention is to provide a surgically implantable drug delivery system comprising a biodegradable polymer, preferably a lactide-co-glycolide copolymer, and an antipsychotic drug, preferably haloperidol, fabricated into an implant via solvent casting and compression molding.

Another object of the present invention is to provide a method of producing surgically implantable drug delivery systems for haloperidol which comprises dissolving the haloperidol and a biodegradable polymer, preferably a lactide-co-glycolide copolymer, in an organic solvent; solvent casting the haloperidol and biodegradable polymer solution; and molding under compression the solvent cast solution into a surgical implant.

Another object of the present invention is to provide a method for treating patients with psychotic conditions and diseases which comprises surgically implanting into a patient suffering from a psychotic condition or disease a surgically implantable drug delivery system comprising a biodegradable polymer, preferably a lactide-co-glycolide copolymer, and an antipsychotic drug, preferably haloperidol, which have been fabricated into an implant via solvent casting and compression molding.

DETAILED DESCRIPTION OF THE INVENTION

The present invention relates to a surgically implantable preparation of an antipsychotic agent such as haloperidol which provides superior treatment outcomes due to improved medication adherence. The surgically implantable preparations of the present invention are designed to last for months to years, providing for symptomatic improvement as well as possibly delaying disease progression for periods of time never before possible. Advantages of administration of antipsychotic drugs via the surgically implantable delivery systems of the present invention include lower dosing and steady state serum drug levels, with fewer resultant side effects. Increased bioavailability with less variation in absorption and no first pass metabolism also decrease variation in plasma levels between individuals for a given dose. These factors promote antipsychotic efficacy with reduced drug exposure and side effects. Additionally, the surgically implantable drug delivery systems of the present invention can be used as a low-dose safety net for relapse prevention, with variable oral dosing of typical or atypical agents for maximum treatment benefit and supplementation during exacerbations. Finally, in the event of unacceptable side effects, such as neuroleptic malignant syndrome, the implant can be removed, thus offering a degree of reversibility not available with depot formulations.

Surgically implantable delivery systems for haloperidol have now been created using biodegradable polymers. In a preferred embodiment, the polymer comprises polylactide or a copolymer comprising polylactide such as a lactide-co-glycolide copolymer. Preferred biodegradable polymers comprise about 50 to 100% polylactide and 0 to 50% polyglycolide. The copolymer and antipsychotic drug, haloperidol, are fabricated into an implant via solvent casting and compression molding. In a preferred embodiment of this method, the individual polymers and haloperidol are dissolved in an organic solvent and solvent cast at a temperature at which the solvent evaporates for a period of time which allows for complete drying of the polymer-drug mixture. For example, for haloperidol and polymers dissolved in acetone, it has been found that solvent casting at a temperature of about 60° C. for approximately 72 hours evaporates all the solvent and results in a completely dry haloperidol-polymer mixture. Complete drying can be assessed by weighing the material at the beginning of solvent casting and at the end of the solvent casting to ensure that all solvent has been evaporated. Haloperidol concentrations preferably range from about 20% to about 40% in the delivery system depending upon the release period. Inclusion of haloperidol in the drug delivery system actually increases the stability of the drug delivery system. Thus, the higher the concentration of haloperidol, the more extended the period of release. This increase in stability does not occur with all drugs. In fact, other antipsychotic drugs such as thiothixene decreased stability and the period of release of the drug delivery system when drug concentrations were increased. Solvent cast material is then compression molded at a temperature and pressure which allows the polymer-drug material to flow into the mold. For example, compression molding at 80° C. and 25,000 psi (density 1.1±0.05 grams/cc) has been demonstrated to be suitable for haloperidol implants of the present invention.

Implants of the present invention were characterized in vitro for release kinetics. Implants comprising 75:25 PLGA with 40% haloperidol resulted in a pattern of release characterized by an initial phase of slow release (mean=0.04 mg/day for an average of 21 mg haloperidol load per implant) from 0 to 28 days. This rate corresponds to approximately 0.21%/day during the first month. A second phase of more rapid release occurred between 28 and 84 days (0.27 mg/day per implant), corresponding to approximately 1.29%/day. Implants comprising 85:15 PLGA with 40% haloperidol displayed a similar pattern of release with a phase of slow release (mean=0.05 mg/day for an average of 21 mg haloperidol load per implant) from 0 to 56 days, corresponding to approximately 0.24%/day during the first 2 months. A second phase of more rapid release occurred between 56 and 140 days (0.23 mg/day per implant), corresponding to approximately 1.1%/day. Release from a theoretical composite system of 75:25 and 85:15 PLGA, 40% haloperidol, shows an early phase from 0 to 28 days with an average of 0.14 mg/day and more rapid release between 28 to 140 days with 0.37 mg/day. Since these values result from an average drug load of approximately 42 mg, the percent released is 0.33%/day during days 0-28 and 0.88%/day during days 28-140. The value for the positive control solution (100 ng/ml) remained stable throughout the period of 140 days. Based on these release rates, a 4 month supply of haloperidol can be delivered via a 500 mg implant of the present invention comprising 40% haloperidol.

Implants of the present invention were also evaluated in vivo in rodents for bioactivity. These measures included behavioral testing with apomorphine stimulated locomotion in mice, and western blot analyses of D2 receptor expression following implantation in rats. For these experiments, implant compositions were developed to create a staged series of implants that release drug for 5 months. Animals treated with haloperidol implants displayed increased striatal D2 receptor expression as well as increased apomorphine stimulated locomotion.

In behavioral testing with apomorphine stimulated locomotion, mice were tested 3 weeks after receiving implants made of 75:25 PLGA alone or 75:25 PLGA with 20% haloperidol. Baseline locomotor activity was measured for twenty minutes. Animals with control implants traveled a mean of 12223±433 cm, while those with haloperidol containing implants traveled an average of 7664±450 cm. Thus, mice with haloperidol implants traveled significantly less distance that the controls (p<0.001). Implants were then removed and all animals were allowed to recover for 48 hours. After recovery, animals received apomorphine 0.5 mg/kg i.p. twenty minutes prior to locomotor testing, which has been shown to increase locomotor activity in mice (Ninan, I. and Kulkarni, S. K. Psychopharmacology (Berl) 1999 142(2):175-81). After apomorphine challenge, animals that had control implants traveled a mean of 4721±476 cm, while those with haloperidol containing implants traveled a mean of 8531±2536 cm. Therefore, following removal of implants and exposure to apomorphine, mice that had haloperidol implants traveled more distance than control mice (p<0.02).

A mean serum level of 26 ng/ml was measured in mice implanted with haloperidol-PLGA pellets one month following implantation.

Western blots of striatal membranes from all rats revealed a band at an apparent molecular weight of approximately 50 kD corresponding to the predicted molecular weight of the full-length D2 receptor protein (Expert Protein Analysis System, Swiss Institute of Bioinformatics, http://www.expasy.ch/; Bunzow et al. Nature 1988 336(6201):783-7). Mean optical density of bands were quantified relative to the corresponding band for haloperidol-treated rats. Results based on three blots yielded a mean±SD relative to density for haloperidol implant-treated rats of 0.90±0.07 for the 50 kD band. The mean±SD relative density for control rats was 0.64±0.02 (p=0.0002, one tail t-test). An additional band of 25 kD was also labeled, likely corresponding to the intracellular portion of the D2 receptor containing the antigenic peptide against which the antibody was raised. Quantification of the 25 kD band yielded a relative density of 0.88±0.12 for haloperidol treated animals and 0.66±0.14 for control animals (p=0.04, one tail t-test).

Implants of the present invention have also been placed in monkeys. Monkeys with implants exhibited motor side effects consistent with haloperidol release within one day of implantation. Haloperidol serum levels in the monkeys were assessed at baseline and days 5, 12, 19, 27, 40 and 55 following implantation. Data are depicted in the following Table.

| Time (days) | Number of Monkeys | Mean | SD |
|---|---|---|---|
| baseline | 3 | 0.00 | 0.00 |
| 5 | 3 | 6.91 | 0.38 |
| 12 | 3 | 5.36 | 1.32 |
| 19 | 3 | 5.30 | 0.48 |
| 27 | 2 | 9.27 | 6.16 |
| 40 | 2 | 21.05 | 8.49 |
| 55 | 2 | 16.71 | 1.74 |

Interestingly, not all pharmaceutical agents nor all antipsychotic agents are amendable to this delivery system. For example, incorporation of the antipsychotic agent thiothixene into the implant requires lowering of the molding temperature by 40° C. and causes an acceleration in degradation of the polymer as opposed to an extension of degradation time as observed with haloperidol. Further, implant comprising thiothixene degraded at room temperature without exposure to an aqueous environment within 6 months. These implants discolored to a yellow shade and liquefied. In contrast, haloperidol implants of the present invention are stable in storage for periods exceeding one year without any signs of discoloration or change in consistency. Incorporation of the anti-depressant Fluoxetine into this delivery system resulted in an implant which caused tissue necrosis in 8 out of 8 mice tested. No tissue necrosis was observed in mice with control, Navane loaded or haloperidol-loaded implants.

Thus, the surgically implantable delivery system of the present invention provides a unique means for the long term delivery of haloperidol.

The delivery systems of the present invention are useful in the treatment of psychotic disorders, particularly disorders such as schizophrenia where patients are oftentimes noncompliant with their medication. The delivery system of the present invention can be surgically implanted into a patient, most preferably under the skin of the patient between the muscle and the dermis, in accordance with well known techniques. Haloperidol released from the bioerodible implant of the present invention maintains its bioactivity and is delivered at steady state concentrations to the patients for periods of five months or more. Implants of the present invention can be used alone or combined with oral supplementation of haloperidol or another antipsychotic drugs for dynamic response to optimum medication levels. Should the patient exhibit unwanted side effects to the haloperidol, the implant can be easily removed.

The following nonlimiting examples are provided to further illustrate the present invention.

EXAMPLES

Example 1

Implant Fabrication

Implants were fabricated through solvent casting and compression molding. Two polymers, 75% polylactide with 25% polyglycolide (75:25 PLGA) and 85% polylactide with 15% polyglycolide (85:15 PLGA) are present in a combined system of release during a 5-month period. Each copolymer has a distinctive period of degradation, which is determined by the ratio of lactide to glycolide and the molecular weight of the resulting molecule produced. An additional polymer of 100% polylactide (PLA) was used for in vivo testing in rats. All polymers (Alkermes Inc., Cincinnati, Ohio), has an inherent viscosity of 0.66-0.8 DL/gram in chloroform and a molecular weight distribution between 120-140 kD. Individual polymers and haloperidol (Sigma, St. Louis, Mo.) were dissolved in acetone and solvent case at 60° C. for 72 hours. Solvent cast material was compression molded at 80° C. and 25,000 psi (density 1.1±0.05 grams/cc).

Example 2

In Vitro Assay

Individual implants were placed in 1 liter of phosphate buffered saline (PBS), pH 7.0 at 37° C. in constant motion. Haloperidol amount was measured by GCMS (National Medical Services, Willow Grove, Pa.). Each assay included negative controls of implants made of polymer alone and a 100 ng/ml haloperidol standard to assess stability of haloperidol in solution over time.

Example 3

Animals

Implants were tested in rats (Harlan, Indianapolis, Ind.) (n=9) and mice (Jackson Labs, Bar Harbor, N. Mex.)(n=16). All animals were housed in an AAALAC accredited animal facility at the University of Pennsylvania. Institutional Animal Care and Use Committee (IACUC) approved all protocols. Animals were maintained with a 12:12 light:dark cycle with all testing and procedures performed during the light cycle.

Example 4

Implantation/Removal Surgery

Mice and rats were anesthetized with ketamine/xylazine (100/10 mg/kg, i.p.). A 1-cm incision was made in the skin on the dorsal aspect of the animal and an implant was placed between dermis and muscle. Removal of implants was performed with identical anesthesia and incision followed by implant retrieval.

Example 5

Behavioral Testing

Bioactivity of haloperidol implants was assessed in mice and rats. Sixteen C57bl/6 mice received implants made of 75:25 PLGA alone (n=8) or 75:25 with 20% haloperidol (n=8) to assess the effects of implants on locomotion. Following three weeks of implantation, total distance traversed was assessed over a twenty-minute period. Implants were then removed and animals allowed to recover for 48 hours prior to retesting 20 minutes after apomorphine challenge (0.5 mg/kg i.p.) (Sigma, St Louis, Mo.).

Example 6

Western Blot

Six Sprague Dawley rats received implants made of PLA with 30-40% haloperidol. Three rats received implants of PLA alone. Implants remained in all animals for three months prior to removal. Seventy-two hours after implant removal, rats were sacrificed and brains rapidly removed, dissected into four regions (cortex, hippocampus, striatum and cerebellum) then frozen in liquid nitrogen. Western blots for quantitative analysis of D2 receptor protein were performed on striatum. Three concentrations of cortex protein from a single animal (2.5, 5 and 10 μg) were run with all blots as an internal control to insure intensity of labeling was within linearity of quantitative software. Only those blots in which the density of samples was within the linear range of internal standards were used for analyses. Western blots were performed using polyclonal antibody, WR-3526, raised against amino acids 272-282 of the D2 receptor protein (Research and Diagnostic Antibodies, Berkeley, Calif.). Striata were homogenized in homogenization buffer (20 mM HEPES, 2 mM EGTA, 1 mM PMSF, 2 μM Aprotinin and 2 mM DTE), followed by a 30-second sonication. Samples were centrifuged 100,000 g for 1 hour at 4° C. Pellets were resuspended and solubilized in homogenization buffer containing 0.1% Triton X-100. Proteins were extracted on ice for 45 minutes with occasional agitation. After extraction, proteins were centrifuged at 30,000 g for 30 minutes at 4° C. Protein samples were prepared with 25% 4× NuPAGE sample buffer plus 10% reducing agent (Invitrogen) and heat shocked at 70° C. for 10 minutes. Samples were separated on a 10% precasted minigel at 200 volts for 50 minutes. Proteins were transferred to PVDF at 30 volts for 1 hour. Blots were blocked with 5% milk TBS (20 mM Tris, pH=7.5, 0.5 mM NaCl), then washed for 15 minutes. Blots were then incubated overnight with anti-D2-receptor antibody, washed with TBS, and incubated with goat-anti-rabbit horseradish peroxidase conjugate (BioRad, 1:4800) for 1 hour. Blots were then incubated with chemiluminescent substrate (Pierce) for 1 minute, wrapped with plastic and exposed to autoradiographic film.

Example 7

Quantification

The intensity of each band was quantified using a densitometer model 7100 and quantitative analysis software (Bio Rad, Hercules, Calif.) and expressed as a ratio to the corresponding band in rat 1 to yield a ratio of intensity (rat 1=ratio of 1). All samples were processed simultaneously on a single blot to allow for quantitative comparisons between conditions.

What is claimed is:

1. A surgically implantable drug delivery system, comprising (a) a biodegradable polymer or copolymer, wherein said biodegradable polymer or copolymer consists essentially of polylactide or lactide-co-glycolide copolymer; and (b) 20 to 40% haloperidol fabricated into an individual, surgically implantable implant via solvent casting and compression molding at a temperature and pressure which allows the haloperidol-polymer material to flow into a mold for the individual, surgically implantable implant which is surgically implanted underneath the skin of a patient, delivers steady state concentrations of haloperidol to the patient for 5 months or more and is removable from the patient in the event the patient exhibits unwanted side effects following implantation.

2. The surgically implantable drug delivery system of claim 1, wherein the biodegradable polymer or copolymer is 50-100% polylactide and 0-50% polyglycolide.

3. A method for treating patients with psychotic conditions and diseases comprising surgically implanting into a patient suffering from a psychotic condition or disease the surgically implantable drug delivery system of claim 1.

4. The method of claim 3, wherein the surgically implantable drug delivery system is implanted under the skin of a patient between the muscle and the dermis.

5. The method of claim 3, wherein the patient is suffering from schizophrenia.

6. The surgically implantable drug delivery system of claim 1, wherein said haloperidol is present in an amount of about 40%.

7. The surgically implantable drug delivery system of claim 1, wherein said haloperidol is present in an amount of about 20%.

8. The surgically implantable drug delivery system of claim 1, wherein said biodegradable copolymer comprises polylactide and polyglycolide in a ratio of 85:15.

9. The surgically implantable drug delivery system of claim 1, wherein said biodegradable copolymer comprises polylactide and polyglycolide in a ratio of 75:25.

* * * * *